(12) United States Patent
Lowinger et al.

(10) Patent No.: US 9,987,028 B2
(45) Date of Patent: Jun. 5, 2018

(54) PARTIALLY COVERED BRAIDED FUNNEL ASPIRATION CATHETER

(71) Applicant: Cook Medical Technologies LLC, Bloomington, IN (US)

(72) Inventors: Johan Lowinger, Bloomington, IN (US); James Merk, Terre Haute, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 109 days.

(21) Appl. No.: 15/010,398

(22) Filed: Jan. 29, 2016

(65) Prior Publication Data

US 2017/0215900 A1    Aug. 3, 2017

(51) Int. Cl.
*A61B 17/221* (2006.01)
*A61B 17/22* (2006.01)

(52) U.S. Cl.
CPC .... *A61B 17/221* (2013.01); *A61B 2017/2215* (2013.01); *A61B 2017/22079* (2013.01)

(58) Field of Classification Search
CPC ............ A61B 17/221; A61B 17/22031; A61B 2017/2215; A61B 2017/22079
See application file for complete search history.

(56) References Cited

U.S. PATENT DOCUMENTS

| 6,221,006 B1 | 4/2001 | Dubrul et al. |
| 6,238,412 B1 | 5/2001 | Dubrul et al. |
| 6,695,858 B1 | 2/2004 | Dubrul et al. |
| 6,699,260 B2 | 3/2004 | Dubrul et al. |
| 7,972,353 B2 | 7/2011 | Hendriksen et al. |
| 2004/0260333 A1 | 12/2004 | Dubrul et al. |
| 2005/0113804 A1 | 5/2005 | von Lehe et al. |
| 2006/0058836 A1* | 3/2006 | Bose ............ A61B 17/22 606/200 |
| 2011/0166637 A1 | 7/2011 | Irwin et al. |
| 2014/0155981 A1 | 6/2014 | Ferrera et al. |

FOREIGN PATENT DOCUMENTS

| WO | 2009077203 A2 | 6/2009 |
| WO | WO 2009077203 A2 | 6/2009 |
| WO | 2009132858 A2 | 11/2009 |
| WO | WO 2009132858 A2 | 11/2009 |

OTHER PUBLICATIONS

Cardinal IP Patent Search Report, dated Jun. 27, 2014.
Partially Covered Braided Funnel Aspiration Catheter, Cardinal IP Patent Search Report, dated Jun. 27, 2014.

* cited by examiner

*Primary Examiner* — Diane Yabut

(74) *Attorney, Agent, or Firm* — Kevin L. Leffel

(57) ABSTRACT

Methods and devices are described for removing a blockage from an anatomical passageway, for example thrombus or clot from a blood vessel. Devices and methods are provided for removing a blockage from an anatomical passageway. For example, a braided funnel is provided that may be placed adjacent a blockage. The braided funnel may be attached to an elongate tube and the blockage may be aspirated through the tube.

20 Claims, 8 Drawing Sheets

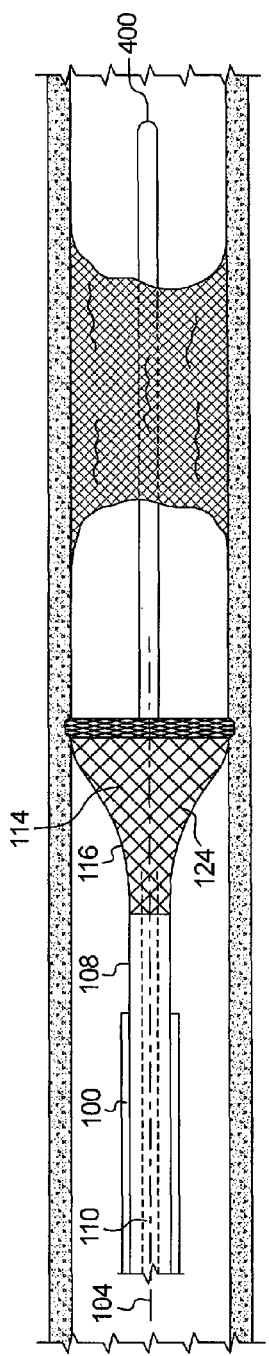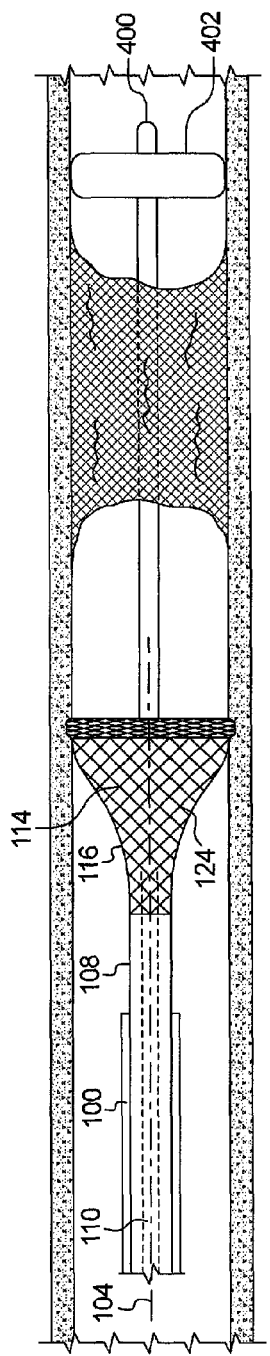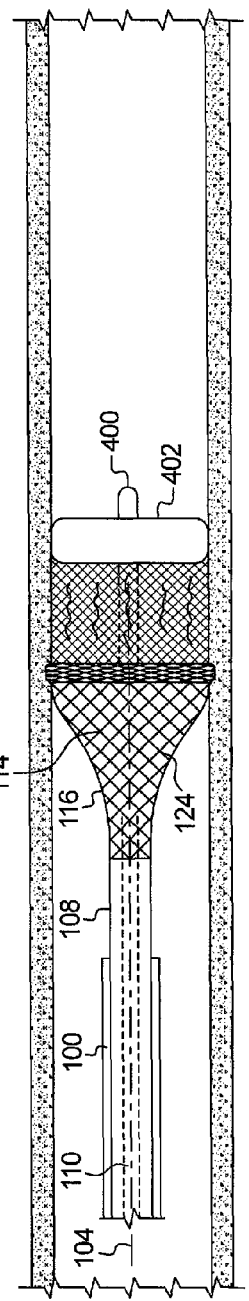

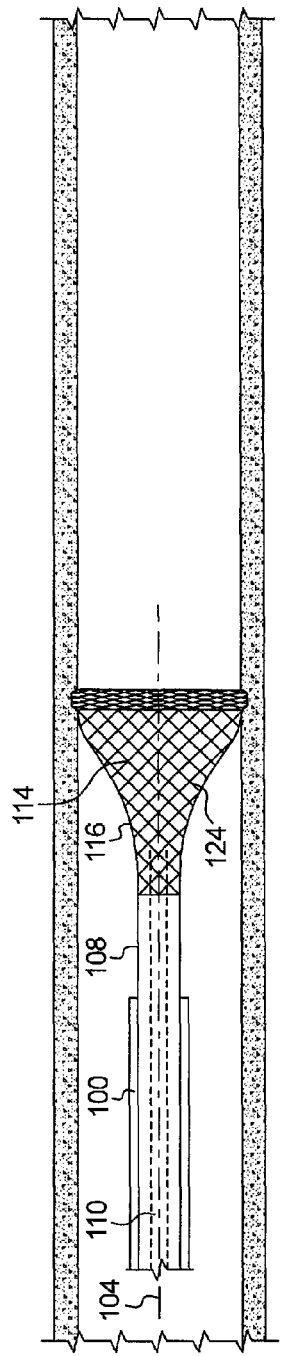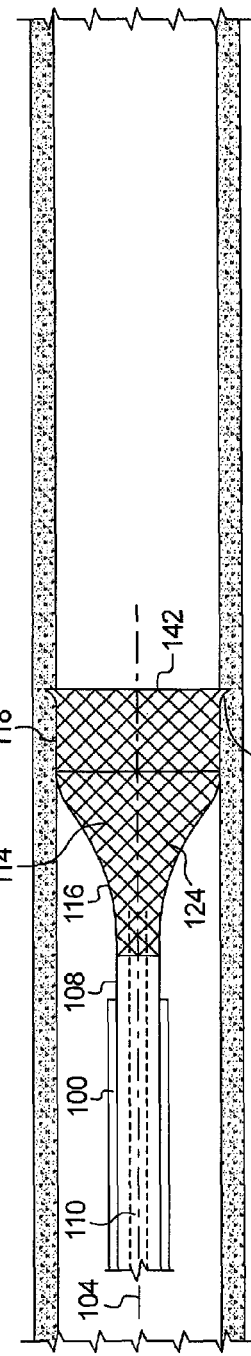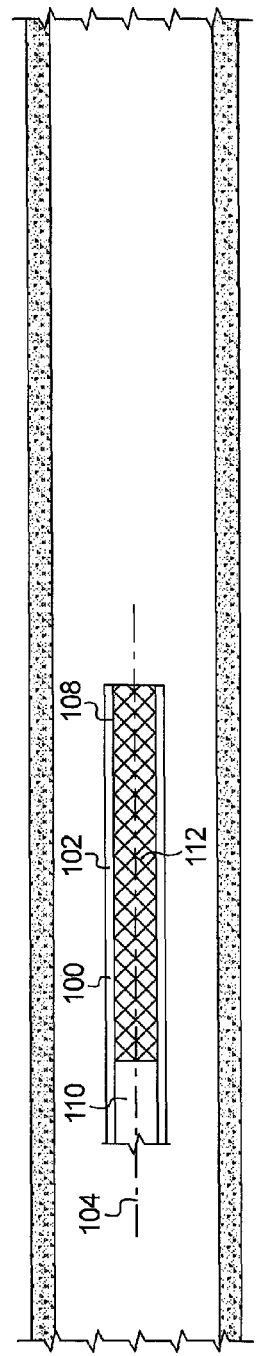

PARTIALLY COVERED BRAIDED FUNNEL ASPIRATION CATHETER

CROSS REFERENCE TO RELATED APPLICATIONS

This application claims the benefit of U.S. Provisional Application Ser. No. 62/115,262, filed Feb. 12, 2015 entitled Partially Covered Braided Funnel Aspiration Catheter, which is hereby incorporated by reference in its entirety.

FIELD

The disclosure generally relates to methods and devices for removing a blockage from an anatomical passageway, for example thrombus or clot from a blood vessel.

SUMMARY

Devices and methods are provided for removing a blockage from an anatomical passageway. For example, a braided funnel is provided that may be placed adjacent a blockage. The braided funnel may be attached to an elongate tube and the blockage may be aspirated through the tube.

BRIEF DESCRIPTION OF THE DRAWINGS

FIG. 9 presents a fourth step in an example of a method;
FIG. 10 presents a fifth step in an example of a method;
FIG. 11 presents a sixth step in an example of a method;
FIG. 12 presents a seventh step in an example of a method;
FIG. 13 presents an eight step in an example of a method; and,
FIG. 14 presents a ninth step in an example of a method.

DESCRIPTION

Figure 1:
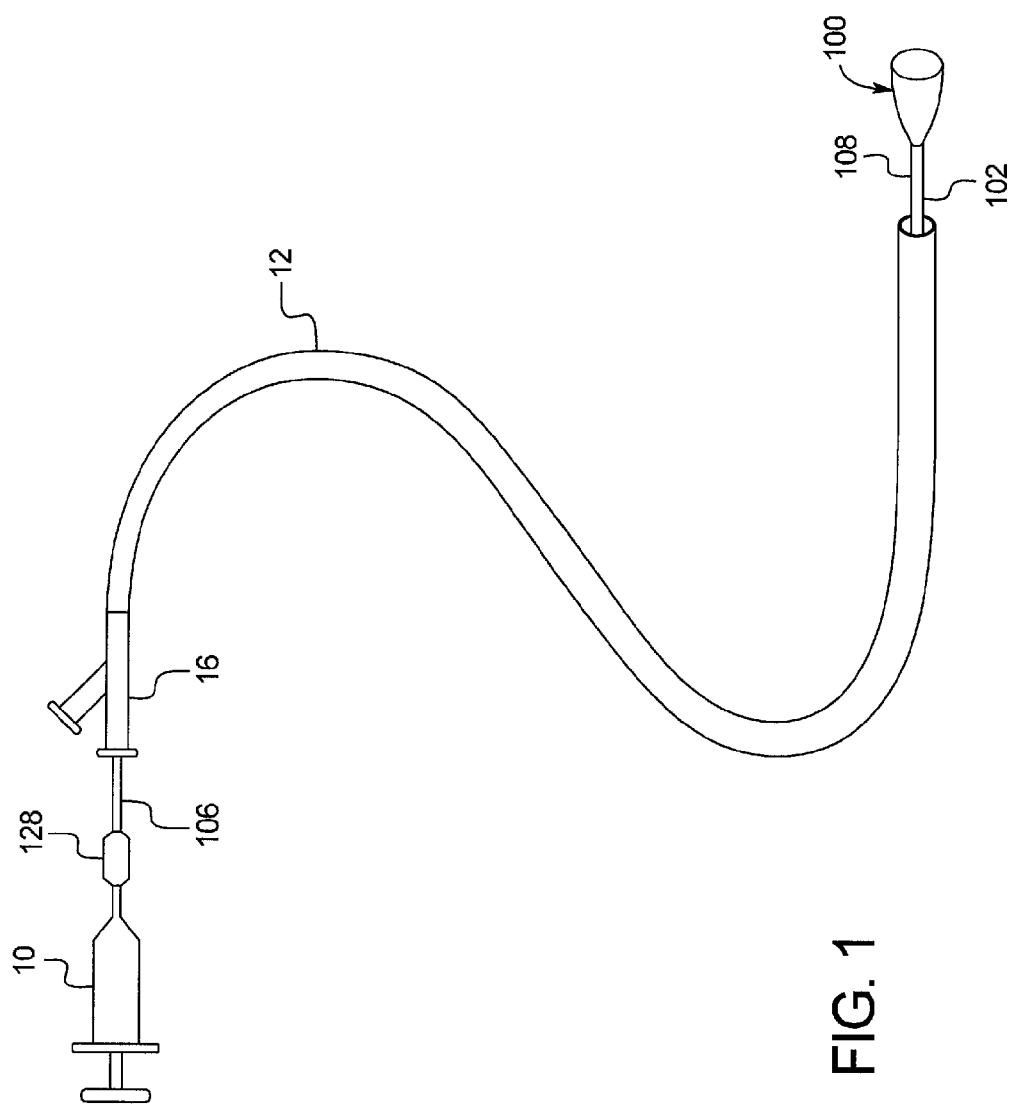
FIG. 1 presents an apparatus according to one example.
Figure 2:
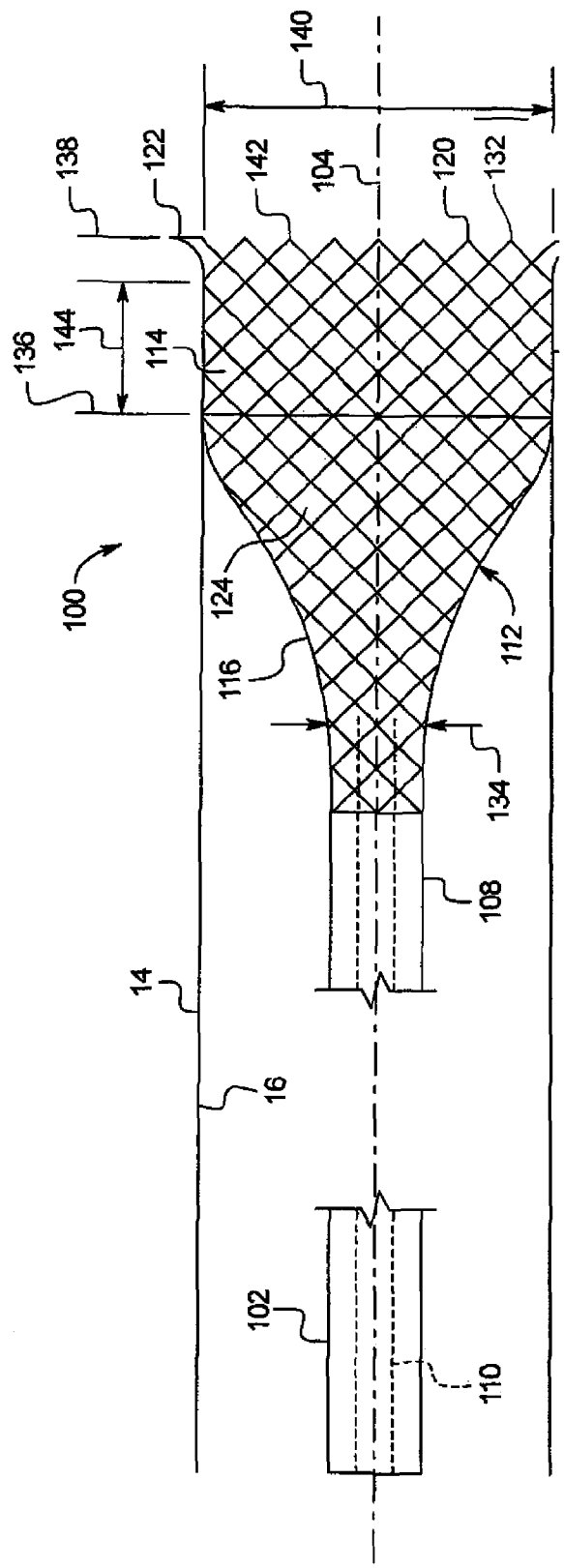
FIG. 2 presents a funnel catheter having a flare on a distal end and closed braid ends in an un-bunched configuration.

Various aspects of the examples are presented in FIGS. 1-14, which are not drawn to any particular scale, and wherein like components in the numerous views are numbered alike. Referring now to FIGS. 1 and 2, a funnel catheter 100 for aspirating a blockage, for example thrombus, from an anatomical passageway is presented. The funnel catheter 100 comprises an elongate tube 102 defining a longitudinal axis 104, a proximal tube end 106, a distal tube end 108, and a lumen 110 along the longitudinal axis 104 from the proximal tube end 106 to the distal tube end 108, the proximal tube end 106 being adapted to attach to an aspiration device 10, for example a syringe. The funnel catheter 100 may also have a braided funnel 112 defining an interior volume 114 and having a proximal funnel portion 116 and a distal funnel portion 118. The proximal funnel portion 116 may be attached to the distal tube end 108 with the lumen 110 in fluid communication with the interior volume 114. The proximal funnel portion 116 may be funnel-shaped with a smallest diameter 134 proximate the distal tube end 108 that approximates the outer diameter of the distal tube end 108. The distal funnel portion 118 defines a distal funnel end 120. The distal funnel end 120 may terminate with a radially outward flare 122. A cover 124 may be provided on the proximal funnel portion 116 but not on the distal funnel portion 118. The cover 124 may completely cover the proximal funnel portion 116.

Figure 3:
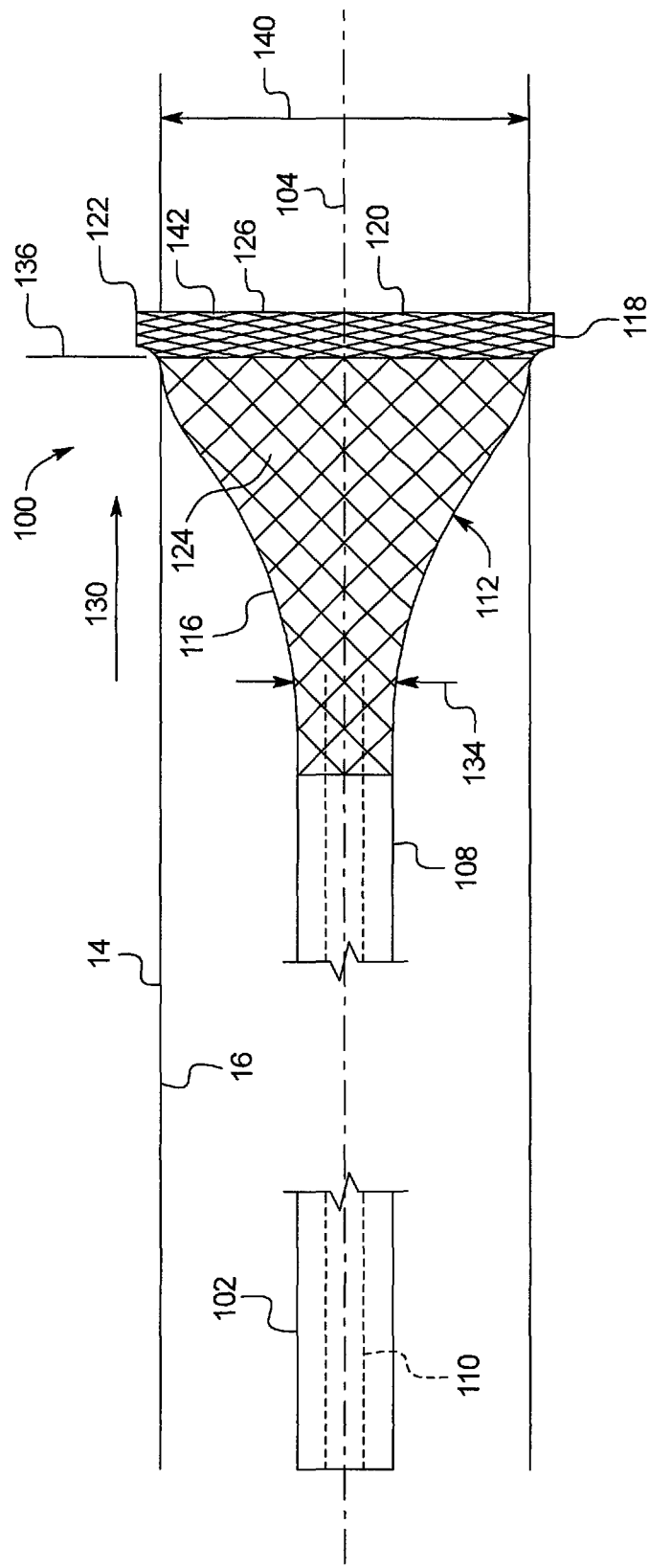
FIG. 3 presents the funnel catheter of FIG. 2 in a bunched-up configuration.

Referring now to FIGS. 2 and 3, the outward flare 122 engages the inside of the anatomical passageway 14 thereby causing the distal funnel portion 118 to axially bunch up against the cover 124 and have an increased radial compression strength relative to an un-bunched configuration. Movement of the braided funnel 112 in the distal direction, indicated by arrow 130, causes the distal funnel portion to bunch-up against the cover 124. For example, after deployment the braided funnel 112 is unconstrained and expands, and the outward flare 122 engages the inside of an anatomical passageway 14. Moving the braided funnel in the distal direction 130 causes the distal funnel portion 118 to axially bunch up against the cover 124 because the outward flare 122 engages the anatomical passageway 14, which fixes the distal funnel end 120 to the wall 16 of the anatomical passageway 14. Further pushing the braided funnel 112 in the distal direction 130 causes it to bunch up (contract) in the longitudinal direction and expand in the transverse direction and have an increased radial compression strength relative to an un-bunched configuration. It forms a ring-like structure 126. The ring-like structure 126 may also increase radiopacity relative to the un-bunched configuration.

An increased radial compression strength is advantageous. The anatomical passageway presses down upon the braided funnel 112 and the increased compression strength resists this better than a conventional braided structure. Also, when removing a blockage, forces may tend to push a conventional braided structure to one side or another. The braided funnel 112 better resists these forces and helps maintain a seal with the wall 132.

The proximal funnel portion 116 may be funnel shaped including generally conical shaped. The distal funnel portion 118 may be a cylinder, or other shape that will bunch up and form a ring-like structure 126, as described above. For example, a shape that complements an artery shape may be desirable. A triangular shape may be desirable a heart valve. An oblong shape may be desirable in vessels with anatomical anomalies, for example where a ligament crosses a blood vessel. As a frame of reference these shapes are in cross-section relative to the longitudinal axis 104.

Referring again to FIG. 1, the sheath 12 is percutaneously inserted into an anatomical passageway 14, for example a blood vessel. The braided funnel 112 and the elongate tube 102 may be disposed within the sheath 12 prior to the sheath 12 being inserted into the anatomical passageway 14. Alternatively, the braided funnel 112 and the elongate tube may be disposed within the sheath 12 after the sheath 12 is inserted into the anatomical passageway 14. The sheath 12 may have a connector 16 on a proximal end and the funnel catheter 100 may pass through the connector 16. The connector may have a hemostatic valve through which the elongate tube 102 and the braided funnel 112 in a collapsed configuration are passed, for example a Touhy Borst adapter or a Captor® hemostatic valve (Cook Medical, Bloomington, Ind., USA). If used in a vein there may not be a need for a seal because pressure is low there is little if any leakage.

The aspiration device 10 may be in fluid communication with the proximal tube end 106. The aspiration device 10 may be attached to the proximal tube end 106 by a fitting 128 for example, which may be a luer fitting. The aspiration device 10 may be for example a vacuum pump, a VacLok® syringe (Merit Medical Systems, South Jordan, Utah, USA) or a mechanically assisted aspiration syringe with a one way check-valve.

Figure 4:
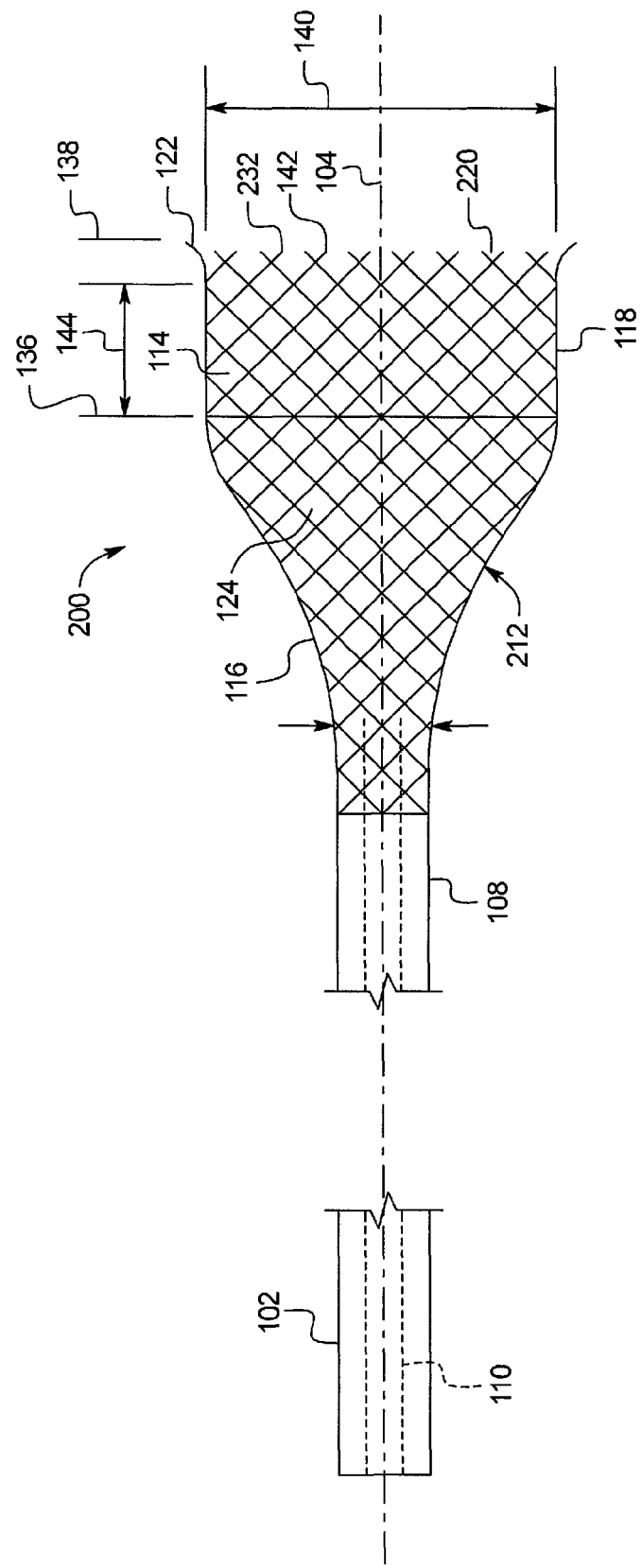
FIG. 4 presents a funnel catheter having a flare on a distal end and open braid ends in an un-bunched configuration.
Figure 5:
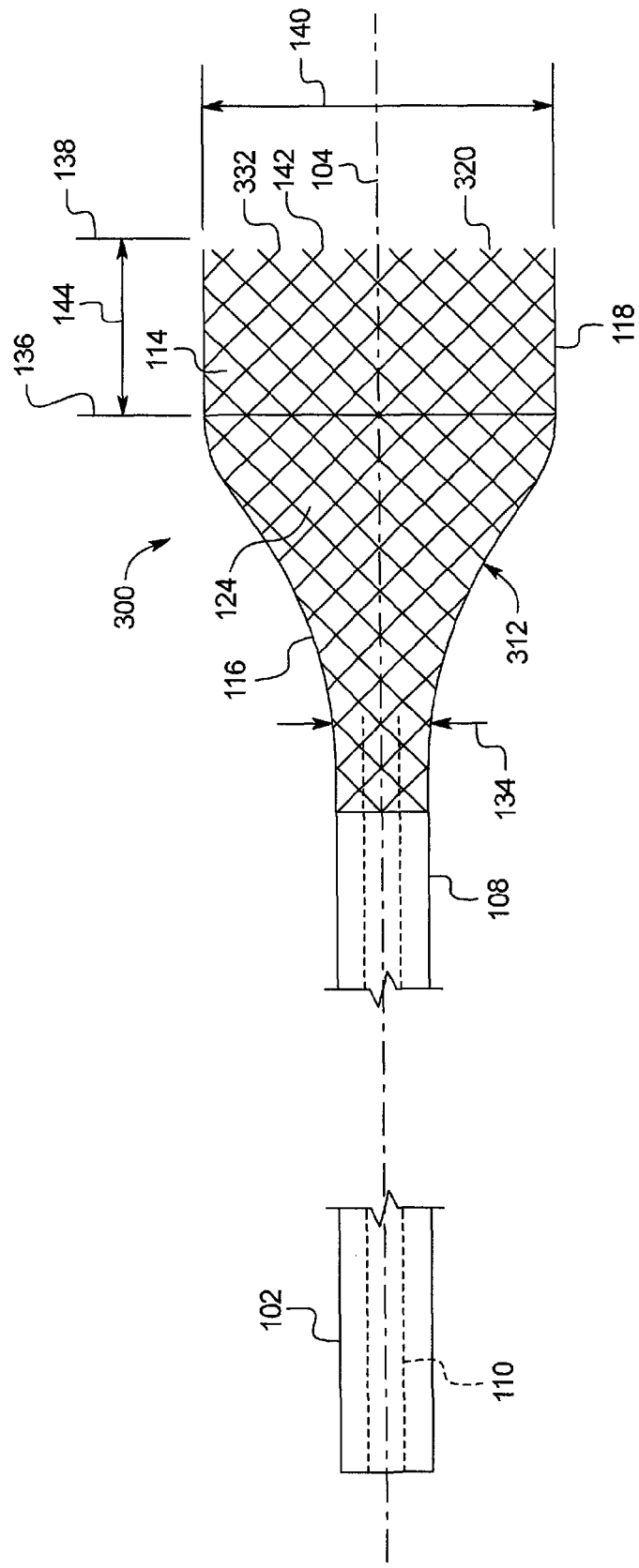
FIG. 5 presents a funnel catheter having open braid ends in an un-bunched configuration.

In FIG. 2, the distal funnel end 120 of the braided funnel 112 comprises closed braid ends 132. The wires bend back into the braid structure. A single wire braid, for example, exhibits this characteristic. Referring to FIG. 4, funnel catheter 200 is presented having a braided funnel 212 wherein the distal funnel end 220 comprises open wire terminations 232 that are exposed wire ends. The exposed wire ends present a rougher surface to the inside of the anatomical passageway 14, which helps keep the distal funnel end 12 from slipping as the braided funnel 112 is moved in the distal direction. FIG. 5 presents a funnel catheter 300 that does not have an outward flare 122 but it comprises a braided funnel 312 wherein the funnel end 320 comprises open wire terminations 332 that are exposed wire ends. As before, the exposed wire ends present a rougher surface that causes the funnel end 320 to engage the inside of the anatomical passageway 14 without the outward flare 122 shown in FIGS. 2 and 3.

As shown in FIGS. 2-5, the cover 124 may completely cover the proximal funnel portion 116. The proximal funnel 116 portion may end at a first plane 136 that may be transverse, for example perpendicular, to the longitudinal axis 104, the cover 124 terminating at the first plane 136. Where the cover 124 terminates may define the location of the first plane 136 along the longitudinal axis 104. The distal funnel portion 118 may terminate at a second plane 138 that may be transverse, for example perpendicular, to the longitudinal axis 104. These features may also be applied to all of the example embodiments described herein and may be implemented alone or in combination.

The braided funnel 112, 212, or 312 may be formed from a wire, for example metals such NiTi, CoCr, stainless steel, and plastics such as PET, Nylon, PEEK Polymide, PTFE, UHMWPE. Metal wires may have a diameter of 0.002 inch to 0.006 inch. Plastic wires may have a diameter of 0.020 inch to 0.060 inch. Of course larger and smaller diameters are contemplated. The elongate tube 102 may be formed from plastic, for example a plastic extrusion. Examples of plastics include nylon and polyurethane without limitation to these materials. The proximal funnel portion 116 may be covered with a thermoplastic material on its proximal end and the braided funnel 112, 212, or 312 may be bonded to the distal tube end 108 by heating the thermoplastic material and fusing the proximal funnel portion 116 to the distal tube end 108.

The distal funnel portion 118 may have a diameter 140 that is 1 mm to 2 mm larger than the inside diameter of the anatomical passageway. The outward flair 122 may a diameter 1 mm to 2 mm larger than the distal funnel portion 118. Alternatively, the diameter 140 may approximate the inside diameter of the anatomical passageway and the outward flair 122 may exceed the diameter 140 by 1 mm to 2 mm. These dimensions are examples and other dimensions are possible depending on the application.

Figure 6:
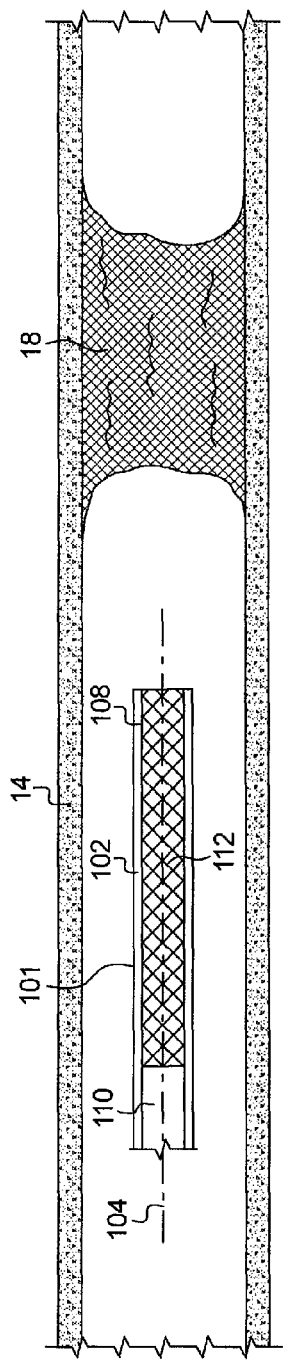
FIG. 6 presents a first step in an example of a method.
Figure 7:
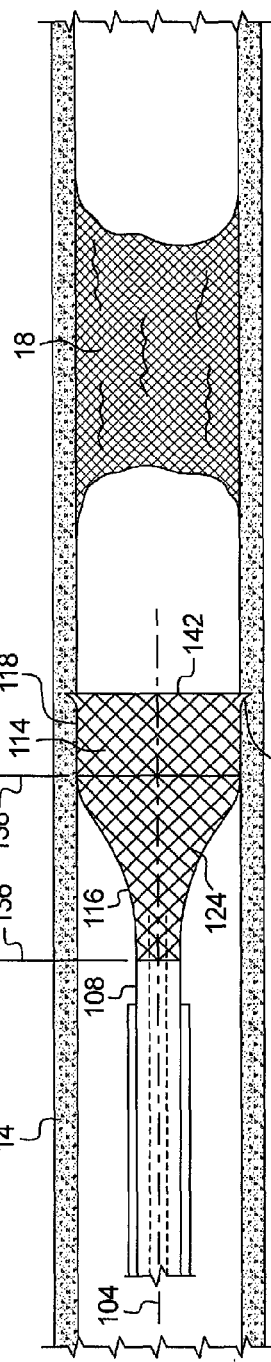
FIG. 7 presents a second step in an example of a method.
Figure 8:
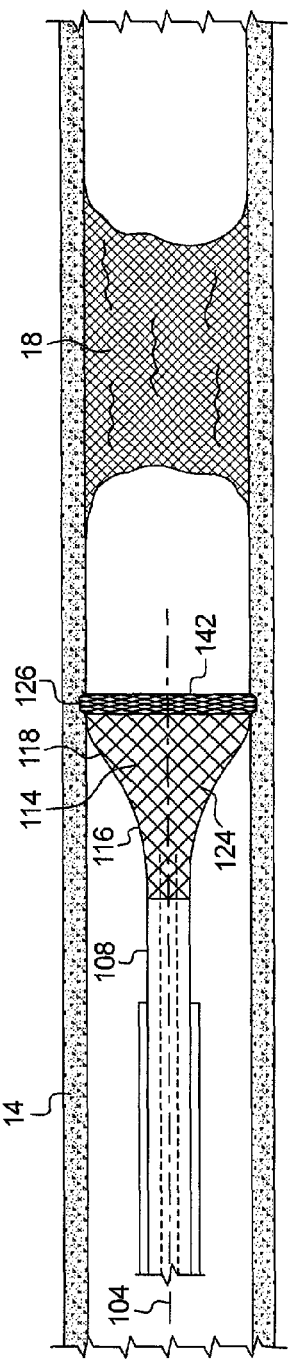
FIG. 8 presents a third step in an example of a method.

Referring now to FIGS. 6 through 14 a method of using a funnel catheter is presented. Although shown with funnel catheter 100, the method may be performed with other funnel catheters, for example funnel catheters 200, or 300. The method comprises inserting the funnel catheter into an anatomical passageway 14, as shown in FIG. 6. Typically, this is done percutaneously. As previously described, the funnel catheter 100 comprises the elongate tube 102 defining the longitudinal axis 104, the proximal tube end 106, the distal tube end 108, and the lumen 110 along the longitudinal axis 104 from the proximal tube end 106 to the distal tube end 108. The braided funnel 112 defines the interior volume 114 and has the proximal funnel portion 116 and the distal funnel portion 118. The proximal funnel portion is attached to the distal tube end 108 with the lumen 110 in fluid communication with the interior volume 114. The proximal funnel portion 116 is funnel-shaped with a smallest diameter proximate the distal tube end 108. The distal funnel portion 118 defines a distal funnel end 120 terminating with a distal braid end 142. There is a cover 124 on the proximal funnel portion 116 but not on the distal funnel portion 118. The cover 124 may completely cover the proximal funnel portion 116. As shown in FIGS. 7 and 8, the method further comprises pushing the elongate tube 102 such that the distal funnel end 120 engages the inside of the anatomical passageway 14 causing the distal portion 118 to axially bunch-up against the cover 124, forming a ring-like structure 126 for example, and have an increased radial compression strength relative to an un-bunched configuration. The thrombus may be removed by applying suction to the lumen 110 of the elongate tube 102, also referred to as aspiration.

With reference to FIG. 9, the method may continue with passing a puller 400, such as a fogarty catheter or other clot removal tools, through the lumen 110 of the elongate tube 102 and through the thrombus 18. The puller 400 has an expandable structure on the distal end that is collapsed during this step. Next, see FIG. 10, the expandable structure 402 is expanded on the distal side of the thrombus 18. The expandable structure 402 may be a balloon, or a braided structure, or other expandable structure suitable for use within an anatomical passageway.

Referring to FIG. 11, a next step may be to use the expandable structure 402 to pull the thrombus 18 toward the braided funnel 112 and into it while applying the aforementioned suction to the lumen 110 of the elongate tube 102 and aspirate the thrombus 12.

FIG. 12 presents the funnel catheter 100 within the anatomical passageway 14 after the thrombus 402 is removed. The expandable structure 402 is subsequently collapsed and may be restrained within its own sheath depending on the type of expandable structure 402 used.

FIG. 13 presents presents another step of pulling the funnel catheter 100 to retract it and bunching the braided funnel 12.

FIG. 14 presents a final step of construing the braided funnel 112 within the sheath 12 for removal from the anatomical passageway 14.

Referring again to FIGS. 6 through 14 another method of using a funnel catheter is presented. Although shown with funnel catheter 100, the method may be performed with other funnel catheters, for example funnel catheters 200, or 300. The method comprises inserting the funnel catheter 100 into an anatomical passageway 14. As previously described, the funnel catheter 100 comprises the elongate tube 102 defining the longitudinal axis 104, the proximal tube end 106, the distal tube end 108, and the lumen 110 along the longitudinal axis 104 from the proximal tube end 106 to the distal tube end 108. The braided funnel 112 defines the interior volume 114 and has the proximal funnel portion 116 and the distal funnel portion 118. The proximal funnel portion 116 is attached to the distal tube end 108 with the lumen 110 in fluid communication with the interior volume 114, the proximal funnel portion 116 is funnel-shaped with a smallest diameter 134 proximate the distal tube end 108.

The distal funnel portion 118 is a cylinder that defines a constant diameter 140 along a length 144 and further defines a distal funnel end 120 terminating with a distal braid end 142. The constant diameter 140 may be from 4 mm to 24 mm depending on the application. It is typically 1 to 2 mm greater than the vessel inside diameter. The outward flair may be 1 to 2 mm.

There is a cover 124 attached to the proximal funnel portion 116. The sheath 12, and the braided funnel 112 and the elongate tube 102 are disposed within the sheath 12. The proximal funnel portion 116 ends at a first plane 136 that may be transverse, for example perpendicular, to the longitudinal axis 104. The covering 114 terminates at the first plane 136. Where the cover 124 terminates may define the location of the first plane 136 along the longitudinal axis 104. The distal funnel portion may terminate at a second plane 138 that may be transverse, for example perpendicular, to the longitudinal axis 104. The method further comprises pushing the braided funnel 112 and the distal tube end 108 out of the sheath, the distal funnel end 120 engaging the inside of the distal anatomical passage 14 causing the distal funnel portion 118 to axially bunch-up against the cover 124 into a ring-like structure and have an increased radial compression strength relative to an un-bunched configuration.

As shown in FIGS. 6 and 7, the method may comprise positioning the braided funnel 112 proximate a thrombus 18 and aspirating the thrombus 18 through the lumen 110. In addition or alternatively, the method may comprise constraining the braided funnel 112 within the sheath 12, as shown in FIG. 14. In addition or alternatively, the method may comprise withdrawing the funnel catheter 100 from the anatomical passageway 14, typically done percutaneously.

Constraining the braided funnel 12 within the sheath may be done at least two ways. The braided funnel 112 may be withdrawn into the sheath 12, or the sheath 12 may be pushed forward over the braided funnel 112.

Various currently contemplated examples follow:

Example 1

With reference to FIG. 2, an example of a funnel catheter such as funnel catheter 100 for aspirating a blockage from an anatomical passageway such as anatomical passageway 14 is provided comprising:
an elongate tube such as elongate tube 102 defining a longitudinal axis such as longitudinal axis 104, a proximal tube end such as proximate tube end 106, a distal tube end such as distal tube end 108, and a lumen such as lumen 110 along the longitudinal axis from the proximal tube end to the distal tube end, the proximal tube end being adapted to attach to an aspiration device such as aspiration device 10;
a braided funnel such as braided funnel 112 defining an interior volume such as interior volume 114 and having a proximal funnel portion such as proximal funnel portion 116 and a distal funnel portion such as distal funnel portion 118, the proximal funnel portion being attached to the distal tube end with the lumen in fluid communication with the interior volume, the proximal funnel portion being funnel-shaped with a smallest diameter such as smallest diameter 134 proximate the distal tube end, the distal funnel portion defining a distal funnel end such as distal funnel end 120 terminating with a radially outward flare such as radially outward flare 122;
a cover a cover such as cover 124 on the proximal funnel portion but not on the distal funnel portion;
wherein the outward flare engages the inside of the anatomical passageway thereby causing the distal funnel portion 118 to axially bunch up against the cover and have an increased radial compression strength relative to an un-bunched configuration.

Example 2

The funnel catheter 100 of Example 1 configured wherein the distal funnel end 120 of the braided funnel 112 comprises closed braid ends 132, as shown in FIG. 2.

Example 3

The funnel catheter of Example 1 may be configured as funnel catheter such as funnel catheter 200 of FIG. 4 wherein the distal portion of the braided funnel such as braided funnel 212 comprises open wire terminations such as open wire terminations 232. It may also be configured as the funnel catheter such as funnel catheter of FIG. 4 where the distal portion of the braided funnel such as braided funnel 312 comprises open wire terminations such as open wire terminations 332. This may be implemented with the elements of Example 2 alternatively or in addition to one another.

Example 4

As shown in FIG. 2, the Funnel catheter of Example 1 may be configured wherein the cover completely covers the proximal funnel portion. This applies to funnel catheter 200 of FIG. 4 and funnel catheter 300 of FIG. 5, for example. This may be implemented with the elements of Examples 2 and 3, either alternatively or in addition to one another.

Example 5

The Funnel catheter of Example 1 wherein the proximal funnel portion ends at a first plane such as first plane 136 that is transverse to the longitudinal axis, the cover terminating at the first plane. This may be implemented with the elements of Example 2, Example 3, and Example 4, either alternatively or in addition to one another.

Example 6

The Funnel catheter of Example 1 wherein the distal funnel portion terminates at a second plane such as second plane 138 that is transverse to the longitudinal axis. This may be implemented with the elements of Example 2, Example 3, and Example 4 either alternatively or in addition to one another.

Example 7

The Funnel catheter of claim Example 1 wherein the proximal funnel portion ends at the first plane that is transverse to the longitudinal axis, the cover terminating at the first plane, and wherein the distal funnel portion terminates at the second plane that is transverse to the longitudinal axis 104. This may be implemented with the elements of Example 2, Example 3, and Example 4 either alternatively or in addition to one another.

Example 8

With reference to FIGS. 6, 7, and 8 a method of using a funnel catheter such as funnel catheter 300, 200, or 100, is provided comprising:

inserting the funnel catheter into an anatomical passageway such as anatomical passageway 14, as shown in FIGS. 6 and 7, the funnel catheter, comprising:

an elongate tube such as elongate tube 102 defining a longitudinal axis such as longitudinal axis 104, a proximal tube end such as proximal tube end 106, a distal tube end such as distal tube end 108, and a lumen such as lumen 110 along the longitudinal axis from the proximal tube end to the distal tube end;

a braided funnel such as braided funnel 312, 212, or 112 defining an interior volume such as interior volume 114 and having a proximal funnel portion such as proximal funnel portion 116 and a such as distal funnel portion distal funnel portion 118, the proximal funnel portion being attached to the distal tube end with the lumen in fluid communication with the interior volume, the proximal funnel portion being funnel-shaped with a smallest diameter such as smallest diameter 134 proximate the distal tube end, the distal funnel portion defining a distal funnel end such as distal funnel end 320, 220, or 120 defining a distal braid end such as distal braid end 142;

a cover such as cover 124 on the proximal funnel portion but not on the distal funnel portion; and, as shown in FIG. 8, pushing the elongate tube such that the distal funnel end engages the inside of the distal anatomical passageway causing the distal portion to axially bunch-up against the cover and have an increased radial compression strength relative to an un-bunched configuration.

Example 9

Example 8, the distal braid end defining a radially outward flare such as radially outward flare 122 in the embodiment of Example 12, as shown 7.

Example 10

Example 8, wherein the bunch-up forms a ring-like structure such as ring-like structure 126, as shown in FIG. 8. This may be used with the elements of Example 9 either alternatively or in addition to one another.

Example 11

Example 8, wherein the distal braid end of Example 12 comprises open wire terminations 332 or 232. This may be used with the elements of Example 9 and Example 10, either alternatively or in addition to one another.

Example 12

With reference to FIGS. 6, 7, and 8 (structure shown also shown in FIGS. 2, 4, and 5) a method of using a funnel catheter such as funnel catheter 300, 200, or 100 is provided, comprising:

inserting the funnel catheter into an anatomical passage way such as anatomical passageway 14, the funnel catheter comprising:

an elongate tube such as elongate tube 102 defining a longitudinal axis such as longitudinal axis 104, a proximal tube end such as proximal tube end 106, a distal tube end such as distal tube end 108, and a lumen such as lumen 110 along the longitudinal axis from the proximal tube end to the distal tube end;

a braided funnel such as braided funnel 312, 212, or 112 defining an interior volume such as interior volume 114 and having a proximal funnel portion such as proximal funnel portion 116 and a distal funnel portion such as distal funnel portion 118, the proximal funnel portion being attached to the distal tube end with the lumen in fluid communication with the interior volume, the proximal funnel portion being funnel-shaped with a smallest diameter such as smallest diameter 134 proximate the distal tube end, the distal funnel portion defining a distal funnel end such as distal funnel end 320, 220, or 120 terminating with a distal braid end such as distal braid end 142;

a cover such as cover 124 on the proximal funnel portion and attached thereto; and, a sheath such as sheath 12, the braided funnel and the elongate tube disposed within the sheath;

wherein the proximal funnel portion ends at a first plane that is transverse to the longitudinal axis, the cover terminating at a first plane such as first plane 137, and wherein the distal funnel portion terminates at a second plane such as second plane 138 that is transverse to the longitudinal axis; and, pushing the braided funnel and the distal tube end out of the sheath, the distal funnel end engaging the inside of the anatomical passage causing the distal funnel portion to axially bunch-up against the cover into a ring-like structure such as ring-like structure 126 and have an increased radial compression strength relative to an un-bunched configuration.

Example 13

Example 12 the distal funnel end defining a radially outward flare such as radially outward flare 122 as shown in FIG. 7 (structure also shown in FIGS. 2 and 4).

Example 14

Example 12 wherein the distal portion of the braided funnel comprises closed braid ends such as closed braid ends 132 as shown in FIG. 2. The elements of this Example 14 may be used with the elements of Example 13, either alternatively or in addition to one another.

Example 15

Example 12 wherein the distal funnel end of the braided funnel comprises open wire terminations such as open wire terminations 332 or 232 (structure shown in FIGS. 4 and 5). This may be used with the elements of Example 13, either alternatively or in addition to one another.

Example 16

Example 12 wherein the proximal funnel portion has an outer surface and the cover completely covers the outer surface as shown in FIG. 7 (structure also shown in FIGS. 2, 4, and 5). This may be used with the elements of Example 13, Example 14, and Example 15, either alternatively or in addition to one another.

Example 17

Example 12 comprising positioning the braided funnel proximate a thrombus such as thrombus 18, as shown in FIGS. 6 through 10, and aspirating the thrombus through the lumen 110, as shown in FIGS. 11 and 12. This may be used with the elements of Example 13, Example 14, Example 15, and Example 16, either in alternatively or in addition to one another.

Example 18

Example 12 comprising constraining the braided funnel and the distal tube within the sheath. This may be used with the elements of Example 13, Example 14, Example 15, Example 16, and Example 17, either alternatively or in addition to one another.

Example 19

Example 12 comprising withdrawing the funnel catheter from the anatomical passageway. This may be used with the elements of Example 13, Example 14, Example 15, Example 16, Example 17 and Example 18 either alternatively or in addition to one another.

Example 20

Example 12 comprising:
positioning the funnel proximate a thrombus and aspirating the thrombus through the lumen, as shown in FIGS. 6 through 12;
constraining the braided funnel within the sheath, as shown in FIG. 14; and,
withdrawing the Funnel catheter from the anatomical passageway.

All features and modifications of the described examples and dependent claims are usable in all aspects of the examples taught herein. Furthermore, the individual features of the dependent claims, as well as all features and modifications of the described examples are combinable and interchangeable with one another.

What is claimed is:

1. A funnel catheter for aspirating a blockage from an anatomical passageway, comprising:
   an elongate tube defining a longitudinal axis, a proximal tube end, a distal tube end, and a lumen along the longitudinal axis from the proximal tube end to the distal tube end, the proximal tube end being adapted to attach to an aspiration device;
   a braided funnel defining an interior volume and having a proximal funnel portion and a distal funnel portion, the proximal funnel portion being attached to the distal tube end with the lumen in fluid communication with the interior volume, the proximal funnel portion being funnel-shaped with a smallest diameter proximate the distal tube end, the funnel defining a distal funnel end terminating with a radially outward flare;
   a cover on the proximal funnel portion but not on the distal funnel portion;
   wherein the outward flare engages the inside of the anatomical passageway thereby causing the distal funnel portion to axially bunch up against the cover and have an increased radial compression strength relative to an un-bunched configuration.

2. The funnel catheter of claim 1 wherein the distal funnel end comprises closed braid ends.

3. The funnel catheter of claim 1 wherein the distal funnel end comprises open wire terminations that are exposed wire ends.

4. The funnel catheter of claim 1 wherein the cover completely covers the proximal funnel portion.

5. The funnel catheter of claim 1 wherein the proximal funnel portion ends at a first plane that is transverse to the longitudinal axis, the cover terminating at the first plane.

6. The funnel catheter of claim 1 wherein the distal funnel portion terminates at a plane that is transverse to the longitudinal axis.

7. The funnel catheter of claim 1 wherein the proximal funnel portion ends at a first plane that is transverse to the longitudinal axis, the covering terminating at the first plane, and wherein the funnel terminates at a second plane that is transverse to the longitudinal axis.

8. A method of using a funnel catheter, comprising:
   inserting a funnel catheter into an anatomical passageway, the funnel catheter comprising:
   an elongate tube defining a longitudinal axis, a proximal tube end, a distal tube end, and a lumen along the longitudinal axis from the proximal tube end to the distal tube end;
   a braided funnel defining an interior volume and having a proximal funnel portion and a distal funnel portion, the proximal funnel portion being attached to the distal tube end with the lumen in fluid communication with the interior volume, the proximal funnel portion being funnel-shaped with a smallest diameter proximate the distal tube end, the distal funnel portion defining a distal funnel end defining a distal braid end;
   a cover on the proximal funnel portion but not on the distal funnel portion; and,
   pushing the elongate tube such that the distal funnel end engages the inside of the distal anatomical passageway causing the distal funnel portion to axially bunch-up against the cover and have an increased radial compression strength relative to an un-bunched configuration.

9. The method of claim 8, the distal braid end defining a radially outward flare.

10. The method of claim 8, wherein the bunch-up forms a ring-like structure.

11. The method of claim 8, wherein the distal braid end comprises open wire terminations that are exposed wire ends.

12. A method of using a funnel catheter, comprising:
    inserting a funnel catheter into an anatomical passage way, the funnel catheter comprising:
    an elongate tube defining a longitudinal axis, a proximal tube end, a distal tube end, and a lumen along the longitudinal axis from the proximal tube end to the distal tube end;
    a braided funnel defining an interior volume and having a proximal funnel portion and a distal funnel portion, the proximal funnel portion being attached to the distal tube end with the lumen in fluid communication with the interior volume, the proximal funnel portion being funnel-shaped with a smallest diameter proximate the distal tube end, the distal funnel portion defining a distal funnel end terminating with a distal braid end;
    a cover on the proximal funnel portion and attached thereto; and,
    a sheath, the braided funnel and the elongate tube disposed within the sheath;
    wherein the proximal funnel portion ends at a first plane that is transverse to the longitudinal axis, the covering terminating at the first plane, and wherein the distal funnel portion terminates at a second plane that is transverse to the longitudinal axis; and,
    pushing the braided funnel and the distal tube end out of the sheath, the distal funnel end engaging the inside of the anatomical passage causing the distal funnel portion to axially bunch-up against the cover into a ring-like structure and have an increased radial compression strength relative to an un-bunched configuration.

13. The method of claim 12, the distal funnel end defining a radially outward flare.

14. The method of claim 12 wherein the distal braid end comprises closed braid ends.

15. The method of claim 12 wherein the distal braid end comprises open wire terminations that are exposed wire ends.

16. The method of claim 12 wherein the proximal funnel portion has an outer surface and the cover completely covers the outer surface.

17. The method of claim 12 comprising positioning the braided funnel proximate a thrombus and aspirating the thrombus through the lumen.

18. The method of claim 12 comprising constraining the braided funnel and the distal tube within the sheath.

19. The method of claim 12 comprising withdrawing the funnel catheter from the anatomical passageway.

20. The method of claim 12 comprising:
   positioning the funnel proximate a thrombus and aspirating the thrombus through the lumen;
   constraining the braided funnel within the sheath; and,
   withdrawing the funnel catheter from the anatomical passageway.

* * * * *